US011725202B2

(12) United States Patent
Buescher et al.

(10) Patent No.: US 11,725,202 B2
(45) Date of Patent: Aug. 15, 2023

(54) SOIL-BASED DNA EXTRACTION

(71) Applicant: Winfield Solutions, LLC, Shoreview, MN (US)

(72) Inventors: Elizabeth Buescher, Ames, IA (US); Brad Roetman, Ames, IA (US); Peter Zervos, Indianapolis, IN (US)

(73) Assignee: WinField Solutions. LLC, Arden Hills, MN (US)

( * ) Notice: Subject to any disclaimer, the term of this patent is extended or adjusted under 35 U.S.C. 154(b) by 179 days.

(21) Appl. No.: 16/165,847

(22) Filed: Oct. 19, 2018

(65) Prior Publication Data

US 2020/0123528 A1   Apr. 23, 2020

(51) Int. Cl.
*C12N 15/10* (2006.01)
(52) U.S. Cl.
CPC .............................. *C12N 15/1006* (2013.01)
(58) Field of Classification Search
CPC .......... C12N 15/1006; C12Q 2523/301; C12Q 2527/125
See application file for complete search history.

(56) References Cited

U.S. PATENT DOCUMENTS

| 6,576,457 | B1 | 6/2003 | Hua | |
|---|---|---|---|---|
| 2004/0259162 | A1* | 12/2004 | Kappel | C12N 15/1006 435/7.1 |
| 2009/0215125 | A1* | 8/2009 | Reed | C12Q 1/6806 435/91.2 |
| 2010/0298162 | A1 | 11/2010 | Kleinfeld et al. | |

(Continued)

FOREIGN PATENT DOCUMENTS

| CN | 1990863 | * | 4/2007 |
|---|---|---|---|
| CN | 1990863 | A | 7/2007 |

OTHER PUBLICATIONS

An Improved Method for Soil DNA Extraction to Study the Microbial Assortment within Rizopsheric Region Faria Fatima, Neelam Pathak, Smita Rastogi Verma Molecular Biology International vol. 2014. (Year: 2014).*

(Continued)

*Primary Examiner* — Brian R Gordon
*Assistant Examiner* — Dwan A Gerido
(74) *Attorney, Agent, or Firm* — Dorsey & Whitney LLP

(57) ABSTRACT

Methods of extracting DNA from soil involve lysing microbial cells contained within the soil by mixing it with an extraction buffer containing cetrimonium bromide (cTAB). The cTAB helps reduce or eliminate high levels of humic acid often present within the soil, which interferes with processes including PCR. Methods further involve binding DNA lysed from the microbial cells and then bound to a silica substrate, washing non-DNA debris from the silica substrate, eluting the DNA from the substrate, and eluting the isolated DNA in an elution buffer. Example methods may involve extracting microbial DNA from a plurality of soil samples. Such methods involve adding soil samples into separate wells within a multi-well plate, lysing microbial cells within the samples using an extraction buffer, binding the microbial DNA released from the cells to silica particles, washing non-DNA debris from the silica particles, and separating the DNA from the silica particles.

20 Claims, 2 Drawing Sheets

(56) References Cited

U.S. PATENT DOCUMENTS

2012/0171728 A1* 7/2012 Wende ............... C12N 15/1006
435/91.2
2013/0260436 A1 10/2013 Ackerley et al.
2014/0099646 A1 4/2014 Connolly et al.

OTHER PUBLICATIONS

Hofinger, Bernhard et al., "Low-cost DNA extraction for recalcitrant plant species version 1.4", Plant Breeding and Genetics Laboratory, Feb. 7, 2013, 7 pages.
Jankowicz-Cieslak, Joanna et al., "Biotechnologies for Plant Mutation Breeding Protocols", Chapter 14—Low-Cost Methods for DNA Extraction and Quantification, 2017, pp. 227-239.
Kathiravan, Mathur N. et al., "Enhanced method for microbial community DNA extraction and purification from agricultural yellow loess soil", Journal of Microbiology; vol. 53, No. 11, 2015, pp. 767-775.
Lipthay, Julia R. et al., "Impact of DNA extraction method on bacterial community composition measured by denaturing gradient gel electrophoresis", Soil Biology & Biochemistry vol. 36, 2004, pp. 1607-1614.
Magana-Arachchi, Dhammika et al., "A Simple and Rapid DNA Extraction Method For Cyanobacteria and Monocots", Cey. J. Sci. (Bio. Sci.) vol. 40, No. 1, 2011, pp. 59-63.
Rojas-Herrera, R et al., "A Simple Silica-based Method for Metagenomic DNA Extraction from Soil and Sediments", Mol Biotechnol, 2008, pp. 13-17.
Seeker, Lulse A. et al., "Method Specific Calibration Corrects for DNA Extraction Method Effects on Relative Telomere Length Measurements by Quantitative PCR", Plos One; DOI:10.1371/journal.pone.0164046, Oct. 10, 2016, 15 pages.
Sun, Lianpeng et al., "Effects of Different Methods of DNA Extraction for Activated Sludge on the Subsequent Analysis of Bacterial Community Profiles", Water Environment Research, vol. 84, No. 2, Feb. 2012, pp. 108-114.
Anderson, "Assessment of DNA Contents of Soil Fungi", vTI Agriculture and Forestry Research, vol. 58, pp. 19-28, 2008.
Lade, et al., "Efficient Genomic DNA extraction Protocol From Medicinal Rich Passiflora Foetida Containing High Level of Polysaccharide and Polyphenol", Springer Plus, vol. 3:457, 7 pages, 2014.
Yeates, et al., "Methods for Microbial DNA Extraction From Soil for PCR Amplification", Biological Procedures Online, vol. 1, No. 1, May 14, 1998, pp. 40-47.
Martin-Laurent, et al., "DNA Extraction from Soils: Old Bias for New Microbial Diversity Analysis Methods", Applied and Environmental Microbiology, vol. 67, No. 5, pp. 2354-2359, May 2001, American Society for Microbiology.

* cited by examiner

SOIL-BASED DNA EXTRACTION

TECHNICAL FIELD

Implementations relate to methods of extracting deoxyribonucleic acid from soil. Particular implementations involve scalable methods of extracting microbial DNA from small to moderately sized soil samples.

BACKGROUND

Genomic DNA from microbial populations present in soil can be extracted and analyzed to acquire species-specific data reflecting a variety of environmental processes. Various approaches to extracting DNA from soil samples have been developed, most of which utilize commercial kits containing proprietary extraction devices and reagents. While such kits can be used to generate large amounts of DNA, large yields are not necessarily desirable for certain applications, the DNA concentrations may be low, and the kit components and corresponding protocols are usually not amenable to user-specific adjustments. As such, the kits may not be scalable and may frequently generate large amounts of wasted products. The kits can also be labor intensive, thus requiring significant time and effort to extract DNA, and protocols developed for other sample types, e.g., plant or human tissue, are not compatible with soil-based DNA extraction techniques. New approaches to extracting microbial DNA from soil samples are thus desired.

SUMMARY

Figure 1:
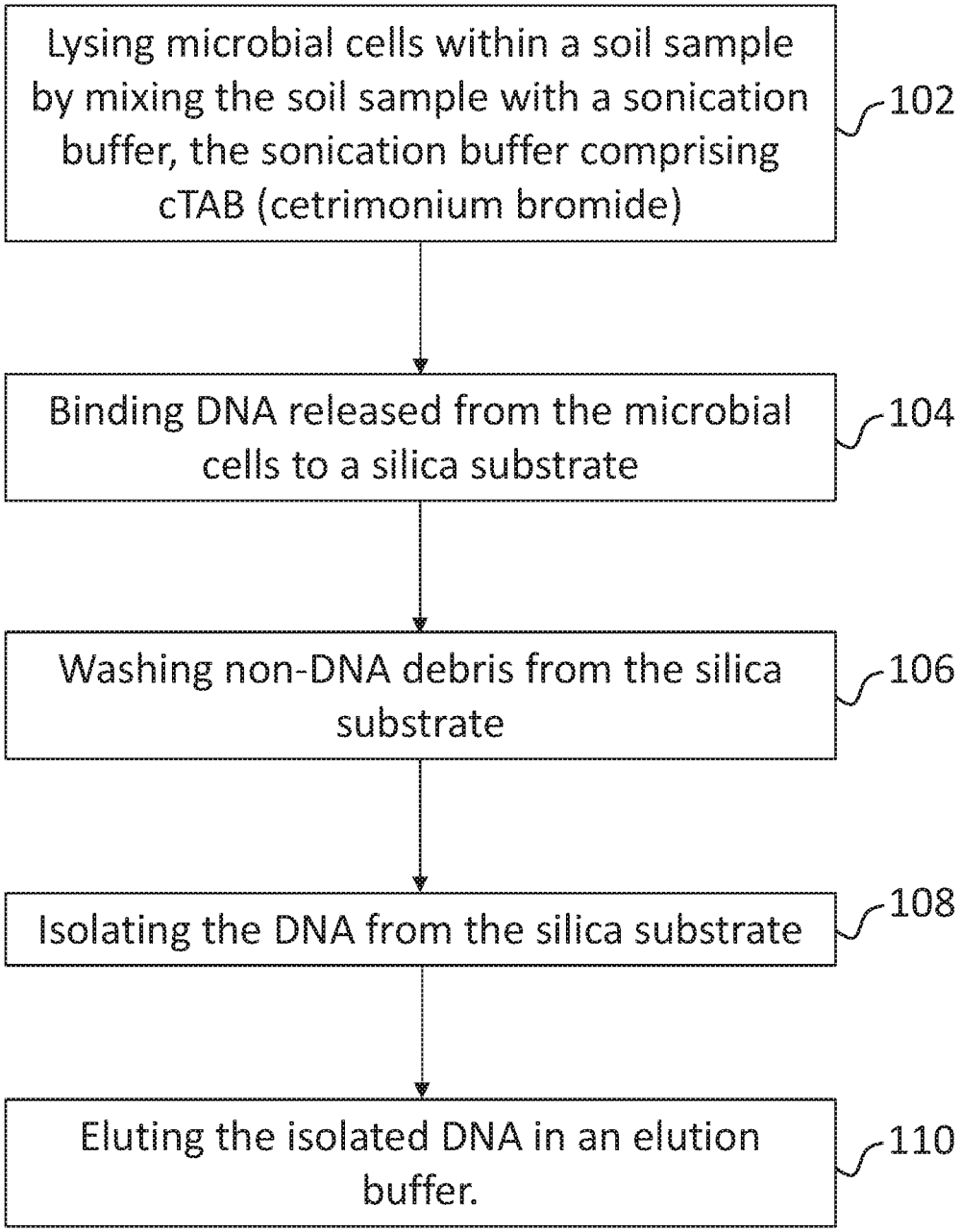
FIG. 1 is a flow diagram of a method performed in accordance with principles of the present disclosure.

Implementations provide methods of extracting genomic DNA from soil. Specific embodiments involve methods and reagents for extracting genomic DNA from microbial populations included in small to moderately sized soil samples. The methods may be readily scaled according to user preferences, and may be implemented using standard laboratory equipment and common laboratory reagents without the need for commercial kits. Example methods may involve lysing microbial cells contained in a soil-water slurry to release DNA therefrom, binding the released DNA using a silica binding solution, washing non-DNA debris from the bound DNA to isolate it, and resuspending the isolated DNA for continued analysis. The final DNA samples may be free or substantially free of humic acid and thus highly pure, thereby improving the effectiveness of PCR-based amplification and analysis.

In accordance with principles of the present disclosure, a method of extracting DNA from a soil sample may involve lysing microbial cells within the soil sample by mixing the soil sample with a sonication buffer, the sonication buffer comprising cTAB (cetrimonium bromide). The method may also involve binding DNA released from the microbial cells to a silica substrate, washing non-DNA debris from the silica substrate, isolating the DNA to the silica substrate, and eluting the bound DNA using an elution buffer.

In some examples, mixing the soil sample with a sonication buffer may be performed in an 8-mL well of a multi-well plate. In some embodiments, the soil sample may include between about 250 and about 750 µg of soil, inclusive. In some examples, the soil sample may include a mixture of soil and water, e.g., a slurry. In some embodiments, about 2 mL of the mixture of soil and water may be mixed with the sonication buffer. In some examples, the silica substrate includes a solution of silica powder and water. In some embodiments, the silica powder and water may be present in the solution at a ratio of 1:1 or about 1:1. In some examples, binding DNA released from the microbial cells to a silica substrate may involve admixing the DNA released from the microbial cells with a mixture of 200 µL (or about 200 µL) of the solution and 1 mL (or about 1 mL) of 6M guanidine thiocyanate.

In some examples, the method can further involve centrifuging the soil sample and the sonication buffer together at about 4816×g (4700 rpm) for about 5 minutes, thereby forming a supernatant containing the DNA released from the microbial cells. In some examples, lysing the microbial cells within the soil sample further involves sonicating the soil sample mixed with the sonication buffer. In some embodiments, washing non-DNA debris from the silica substrate involves resuspending and centrifuging the silica substrate in a wash buffer two or more times. In some embodiments, the sonication buffer may include about 2% w/v cTAB.

In accordance with principles of the present disclosure, a method of extracting microbial DNA from a plurality of soil samples can involve adding 2 mL (or about 2 mL) of each of the plurality of soil samples into separate wells within a multi-well plate and lysing microbial cells within each of the plurality of soil samples by mixing each soil sample with a sonication buffer, the sonication buffer comprising cTAB. The method may further involve binding the microbial DNA released from the microbial cells to silica particles suspended in a silica solution, washing non-DNA debris from the silica particles, and eluting the DNA from the silica particles to obtain isolated DNA.

In some examples, each of the separate wells within the multi-well plate holds 8 mL of liquid (or about 8 mL). In some embodiments, the multi-well plate includes 24 wells (or about 24 wells). In some examples, the sonication buffer comprises NaCl, PVP, TE buffer, RNase A, and about 2% w/v cTAB. In some embodiments, each of the plurality of soil samples comprises a 1:1 mixture of soil and water (or about 1:1). In some examples, each of the plurality of soil samples comprises about 500 µg of soil (or about 500 µg). In some embodiments, binding the microbial DNA released from the microbial cells to silica particles comprises admixing the microbial DNA with a mixture of 200 µL of the silica solution and 1 mL of 6M guanidine thiocyanate. In some examples, the silica solution includes a 1:1 mixture of silica particles and water (or about 1:1).

DETAILED DESCRIPTION

The soil-based DNA extraction methods provided herein can advantageously utilize a smaller amount of soil compared to preexisting methods and may reduce, minimize or eliminate humic acid content within the soil samples during extraction, thereby improving final DNA purity. The methods may also be scaled as desired to meet user preferences, making the methods adaptable to a variety of different applications, e.g., research and industrial. The final genomic DNA products may be highly concentrated and pure. The equipment required to implement the methods may be standard equipment typically found in most research or production laboratories. Specialized devices, such as the disposable bead tubes, membranes and spin columns frequently included in commercial kits, are not required to perform the methods herein, thereby providing additional benefits related to cost expenditures, accessibility and waste.

Extraction methods provided herein may involve multiple stages, which may generally include: lysis, DNA binding, washing and elution stages, with each stage comprising a plurality of steps. Methods may also involve a pre-processing stage. The lysis stage breaks apart the microbial cells included within the soil samples, thereby exposing the internal cellular components, including total genomic DNA. The DNA binding stage causes DNA molecules released from the lysed cells to bind with silica particles included in a DNA binding solution. The washing stage removes extraneous, i.e., non-DNA, soil debris, residual chemicals required in DNA extraction, and cellular components, including lipids, proteins and organelles, etc. The elution stage resuspends the isolated DNA in an elution buffer for quantification and follow-up analysis.

Reagents:

Prior to performing one or more of the aforementioned stages, one or more of the reagents utilized in the extraction process may be prepared and optionally stored. Reagents utilized according to the methods herein may include NaCl, Tris-EDTA, sodium acetate, a wash buffer, a DNA binding buffer, a sonication buffer, a DNA elution buffer, and a DNA binding solution. The specific volumes, concentrations and/or pH levels provided herein for each reagent may be for example purposes only, and should not be viewed as limiting. For example, the amount and/or properties of one or more reagents may be modified according to user preferences such that the disclosed methods are fully scalable. In some embodiments, for example, the volumes of one or more stock reagents may be multiplied to accommodate more plates utilized for an extraction. Stock solutions having higher concentrations than those disclosed below, for example, may be prepared and diluted upon use. In addition, the total volume of each reagent can be readily adjusted depending on the number of soil samples simultaneously used for DNA extraction.

In some examples, the NaCl (sodium chloride) may be 5M (or about 5M), having a molecular weight of 58.44 g/mol. To prepare 5M NaCl, 146.1 grams of NaCl (or about 146.1 grams) may be mixed with distilled water to reach a total volume of 500 mL (or about 500 mL).

In various examples, 10× Tris-EDTA (ethylenediamine tetraacetic acid or "TE") (or about 10×) may be prepared by mixing 100 mL of 1M Tris-HCl, pH 8.0 (or about 100 mL) with 20 mL of 0.5M EDTA, pH 8.0 (or about 20 mL of about 0.5M EDTA) and adding distilled water to reach a total volume of 1 L (or about 1 L).

The sodium acetate may be 3M (or about 3M), having a molecular weight of 82.03 g/mol. To prepare the sodium acetate, 123.05 grams of sodium acetate (or about 123.05 grams) can be mixed with water to reach a total volume of 500 mL (or about 500 mL). The pH may then be adjusted to 5.2 (or about 5.2), for example using glacial acetic acid.

The wash buffer can include 0.05M NaCl (or about 0.05M) and may comprise 90% ethanol (or about 90%). The wash buffer may be prepared by mixing 3 mL of 5M NaCl (or about 3 mL of about 5M NaCl) with 270 mL of 100% ethanol (or about 270 mL of about 100% ethanol) and adding distilled water to reach a total volume of 300 mL (or about 300 mL).

The DNA binding buffer may comprise 6M guanidine thiocyanate (or about 6M), having a molecular weight of 118.2 g/mol. To prepare the DNA binding buffer, 70.92 grams of the 6M guanidine thiocyanate (or about 70.92 grams of about 6M guanidine thiocyanate) can be mixed with distilled water, reaching a total volume of 100 mL (or about 100 mL).

The sonication buffer can comprise 0.5M NaCl (or about 0.5M), 3% PVP (or about 3%) (polyvinylpyrrolidone, weight 40,000), 10×TE (or about 10×), RNase A, and cTAB (cetrimonium bromide), and it may be prepared by mixing 25 mL of 5M NaCl (or about 25 mL of about 5M NaCl) with 7.5 grams of PVP (or about 7.5 grams), and 2% w/v cTAB (or about 2% w/v), and adding 10×TE (or about 10×) up to a total volume of 250 mL (or about 250 mL). The RNase A may be added just prior to use of the sonication buffer. In embodiments, about 50 μL of RNase A at a concentration of 5 μg/L may be added per 50 mL of sonication buffer. The sonication buffer may specifically exclude additional reagents, including proteinase K, SDS (sodium dodecyl sulfate), and various enzymes, e.g., lysozymes and glusulase, thereby further simplifying the processes described herein.

The DNA elution buffer can comprise 0.1× Tris-EDTA (or about 0.1×), which may be prepared by mixing 2 mL of 10× Tris-EDTA (or about 2 mL of about 10× Tris-EDTA) with 48 mL of distilled water (or about 48 mL).

The DNA binding solution utilized herein, which may include a combination of silica powder and water, may replace the commercial binding solutions and associated devices commonly included in commercial kits. Preparation of the DNA binding solution can involve washing and suspending silica powder with water one or more times, e.g., 2, 3, 4 or more times. In one embodiment, about 800 mg of silica powder, e.g., CELITE® 545, can be poured into a 50 mL centrifugation tube, e.g., a BD FALCON™ tube, such that the powder reaches to about the 2.5 mL mark on the tube. About 30 mL of water, which may be distilled, can be added to the tube and mixed with the silica powder by vigorously shaking and/or vortexing. The resulting slurry may then be allowed to settle for approximately 15 minutes, or at least until the powder and water separate. The water can then be decanted and another aliquot of about 30 mL of water added to the silica powder. The aforementioned washing steps, i.e., mixing, separating and decanting, can then be repeated two or more times. After the final washing step, the silica powder can be resuspended in a fresh aliquot of water. The volume of water used to resuspend the silica may vary. In some examples, the volume of water may be approximately equal to the volume of silica, such that the ratio of silica to water is about 1:1 and the resuspension fills about 5 mL of the centrifuge tube. The finished DNA binding solution can be stored at about room temperature, e.g., 20-25° C., until further use. The DNA binding solution may comprise silica and water, only, without any additional components, such as potassium iodide. The simplified solution may provide yet another advantage over preexisting systems.

Immediately prior to use, the DNA binding solution can be resuspended by manually shaking, pipetting and/or vortexing. About 200 μL of the DNA binding solution can then be transferred, e.g., pipetted, into each of one or more wells defined by a multi-well plate. The capacity of each well can be 8 mL in some embodiments, and the number of wells included in the plate may be 24, although the number of wells is not critical. For example, the capacity of each well in a 96-well plate can be 2 mL. Other wells within a multi-well plate may have a 10 mL capacity. The number of wells needed, whether in one plate or multiple, depends on the number of soil samples evaluated, as each soil sample is assigned to one well. Because the methods disclosed herein do not rely on predefined kits, which can only be used to process a limited number of samples simultaneously, the number of soil samples can be scaled up or down as desired by a user, limited only by the number of multi-well plates available and/or the number of plates that can fit in a centrifuge. For example, DNA from about 84 separate soil samples can be simultaneously extracted according the methods herein, such that about 500 samples can be reasonably extracted by one user in one day. This marks a significant improvement over preexisting methods, which may be limited to about 25 samples per user per day. In addition, the multi-well plates can be washed and reused. For instance, plates may be re-washed after each extraction.

During the transfer of DNA binding solution to each well, the remaining stock solution may be periodically agitated to maintain uniform distribution of the silica in the suspension. To each well containing DNA binding solution, 1 mL of the DNA binding buffer can then be added and used to resuspend the silica. Resuspension can be achieved by pipetting (repeatedly up and down) the mixture of DNA binding solution and buffer.

Pre-Processing Stage:

Methods herein may not be limited to a particular soil composition type, and thus may be amenable to soils of varying moisture levels, including soil with various levels of sand, silt, clay, peat, organic matter, etc. One or more soil pre-processing steps may be implemented before the lysis stage. For example, unlike preexisting approaches that may utilize dry soil, methods herein may utilize slurries of soil and water. As such, a pre-processing step can involve wet-milling the soil sample(s) used for DNA extraction. Wet-milling the soil may involve mixing, e.g., blending, the soil with water to form a slurry. Replicates of each soil sample can be prepared, along with one or more control samples. The amount of soil used to prepare each slurry sample may vary, and may be less than amounts required for preexisting DNA extraction protocols, which may recommend about 10 grams of soil per sample. In various embodiments, the amount of soil used to create a slurry for each sample can range from about 250 mg to about 1 gram, about 350 mg to about 750 mg, about 450 mg to about 550 mg, about 475 mg to about 525 mg, or about 500 mg. In some examples, dried, ground soil may still be used. Such examples may be performed with some variations, e.g., without the use of silica as a binding agent.

Lysis Stage:

The lysis stage bursts, punctures and otherwise breaks apart microbial cells present within the soil samples, thereby exposing the internal cellular components, including total genomic DNA, organelles, proteins, etc. During the lysis stage, samples of each slurry, for example about 2 mL, can be pipetted into each well of the multi-well plate(s). To each well, 2.5 mL of sonication buffer can then be added and the plate(s) sonicated for about 30 seconds to about 2 minutes to lyse the cells within the slurry. In some embodiments, RNase A may be added to the sonication buffer just prior to sonication. For example, about 50 µL of RNase A at a concentration of 5 µg/L may be added per 50 mL of sonication buffer, such that 12.5 µg of RNase A are added to each well upon addition of 2.5 mL sonication buffer. The sonication settings applied to the samples may vary. In one example, the plate(s) can be sonicated using a 117V VWR® Ultrasonic Cleaner. The inclusion of cTAB within the sonication buffer, for example at about 2% w/v, can precipitate humic acid and humic acid aggregate components during sonication, facilitating the removal of such substances, which may otherwise contaminate the isolated DNA and inhibit downstream analysis, e.g., PCR. After sonication, 1 mL of 3M sodium acetate can be added to each well, followed by optional mixing, and each plate placed in freezer set at −20° C. for 10 minutes. The plates may then be removed from the freezer and centrifuged at 4816×g (4700 rpm) for 5 minutes at room temperature, thereby separating the released cellular components and DNA (supernatant) from the solid soil debris. The lysis stage may be performed without the use of any metal beads and/or grinding.

DNA Binding Stage:

The DNA binding stage causes DNA molecules released from the lysed cells to bind with DNA-binding particles, such as the silica particles included in the DNA binding solution. The DNA binding stage may first involve preparing 1.2 mL (or about 1.2 mL) of a fresh mixture of DNA binding solution and DNA binding buffer for each soil sample, which can be added to each 8-mL well in a clean multi-well plate. Each aliquot of the fresh mixture can comprise 200 µL (or about 200 µL) DNA binding solution and 1 mL (or about 1 mL) of DNA binding buffer. The supernatant generated during centrifugation of the lysed cells can then be added to each well containing the 1.2-mL aliquot of DNA binding mixture. For each sample, the volume of supernatant removed after centrifugation and combined with DNA binding mixture may be about 4 mL. Care should be used to ensure that no soil is transferred with the supernatant. Each plate may then be covered with a paraffin film, e.g., PARAFILM, and stacked using metal stacking plates, if necessary. Stacked plates may be connected, e.g., via clamps. The covered plates can then be incubated for about 15 minutes at room temperature on a shaker set at 200 rpm. After 15 minutes, the paraffin film can be removed, and the plates centrifuged at or about 4816×g (4700 rpm) for 5 minutes at room temperature, thereby forming a pellet comprised of DNA-bound silica and a liquid supernatant in each well. The supernatant can be removed, e.g., using a pipette, such that only the DNA-bound silica pellet remains in each well. Non-DNA components that remain associated with the silica can be removed during the washing stage.

Washing Stage:

The washing stage removes extraneous, i.e., non-DNA, soil debris, residual extraction chemicals, and cellular components, including proteins, organelles, lipids, membranes, etc., from the silica particles. The washing stage may involve adding 1 mL of wash buffer to each well containing a DNA-bound silica pellet and resuspending the pellet therein. Resuspending the pellet components can involve gently shaking each plate against a table, for example. The resuspension can then be centrifuged at or about 1962×g (3000 rpm) for 1 minute at room temperature. The wash buffer supernatant generated via centrifugation can be removed by pipetting, and the washing step can be repeated using a fresh aliquot of 1 mL wash buffer. After a second round of centrifugation, the supernatant can again be removed via pipette. To remove as much supernatant as possible, the plates can be tipped at an angle, thereby pooling any residual liquid in each well for pipette removal. The DNA-bound silica pellets can be washed 2 or more times, e.g., 3, 4 or 5 times. After the final washing step, the DNA-bound silica can be allowed to dry in a vacuum hood for up to about 1 hour at room temperature.

Elution Stage:

The elution stage elutes the isolated DNA in a buffer, such as the elution buffer described herein. The elution stage can involve adding 300 µL (or about 300 µL) of the DNA elution buffer to each well containing dried silica, and optionally pipetting to mix. The mixture of DNA elution buffer and silica can then be incubated for about 20 minutes at room temperature under gentle agitation, for example by placing the samples on a shaker set at or about 200 rpm. The plates should be kept facing up to keep the silica positioned at or near the bottom of each well. After incubation, the plates can be centrifuged at or about 4816×g (4700 rpm) for 5 minutes at room temperature to pellet the silica, thereby separating the silica from the DNA contained in the elution buffer. About 200 µL of the supernatant can then be removed from each well and placed in a fresh well. Care should be taken to avoid transferring any of the silica with the supernatant, which contains the isolated DNA.

One or more post-extraction steps may then be implemented to analyze the quantity, quality and/or identity of the isolated DNA. For example, each DNA sample can be quantified using a DNA quantification plate reader, e.g., a SPECTROSTAR® Nano reader sold by BMG Labtech. The DNA can be stored at −20° C. for long-term storage or 4° C. for shorter term storage.

FIG. 1 is a flow diagram of an example method 100 of extracting DNA from a soil sample performed in accordance with principles of the present disclosure. The example method 100 shows the steps that may be implemented, in any sequence, to extract DNA from any soil sample by lysing the microbial cells therein, binding the released DNA, washing away non-DNA components, isolating the DNA, and optionally resuspending and eluting the DNA. In additional examples, one or more of the steps shown in the method 100 may be supplemented or omitted.

In the example shown, the method 100 begins at block 102 by "lysing microbial cells within a soil sample by mixing the soil sample with a sonication buffer, the sonication buffer comprising cTAB (cetrimonium bromide)." The method 100 continues at block 104 by "binding DNA released from the microbial cells to a silica substrate." The method 100 continues at block 106 by "washing non-DNA debris from the silica substrate." The method 100 continues at block 108 by "isolating the DNA from the silica substrate." The method continues at block 110 by "eluting the isolated DNA in an elution buffer."

Figure 2:
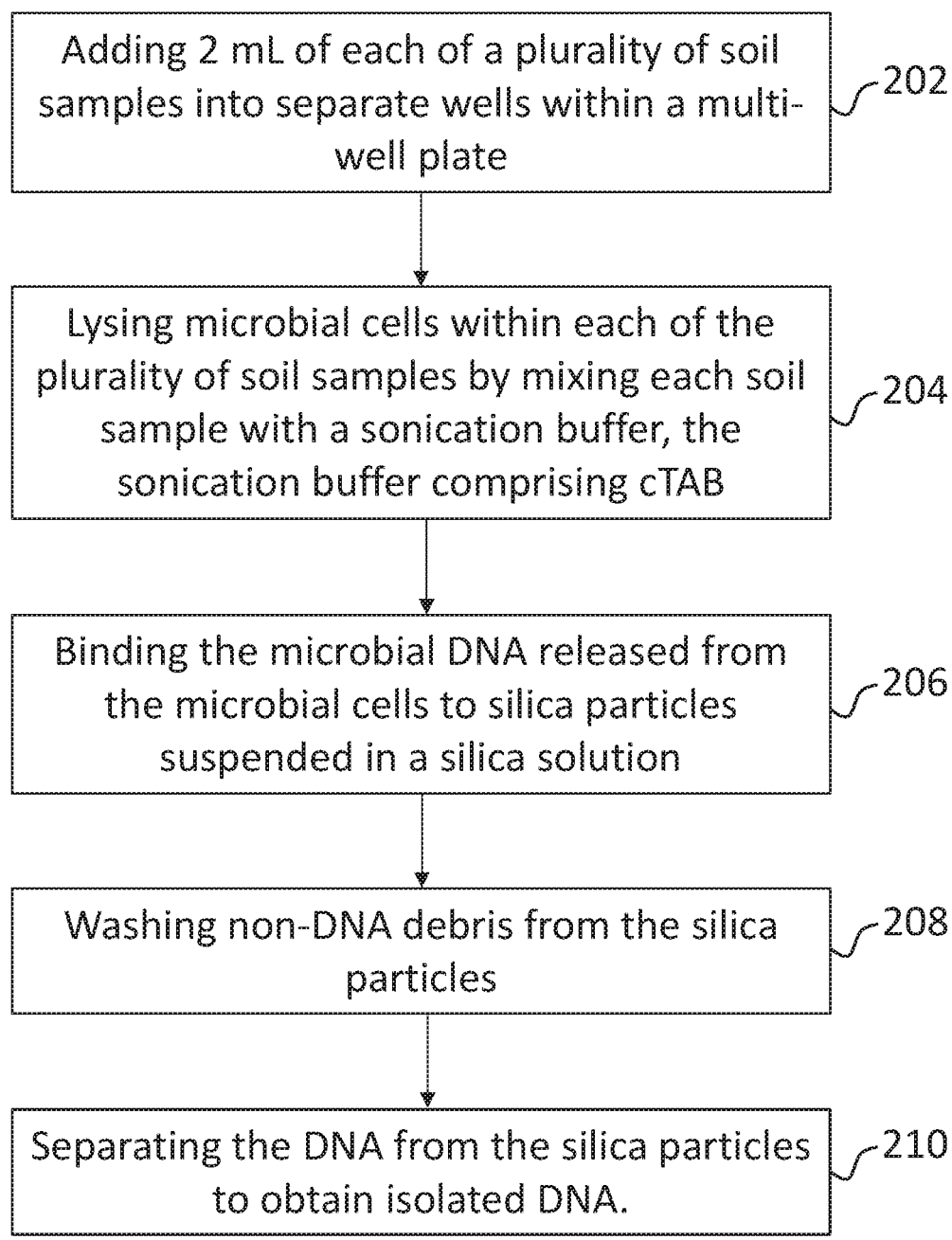
FIG. 2 is a flow diagram of another method performed in accordance with principles of the present disclosure.

FIG. 2 is a flow diagram of an example method 200 of extracting DNA from a plurality of soil samples simultaneously. In additional examples, one or more of the steps shown in the method 200 may be supplemented, rearranged, or omitted.

In the example shown, the method 200 begins at block 202 by "adding 2 mL of each of a plurality of soil samples into separate wells within a multi-well plate." The method 200 continues at block 204 by "lysing microbial cells within each of the plurality of soil samples by mixing each soil sample with a sonication buffer, the sonication buffer comprising cTAB." The method continues at block 206 by "binding the microbial DNA released from the microbial cells to silica particles suspended in a silica solution." The method continues at block 208 by "washing non-DNA debris from the silica particles." The method continues at block 210 by "separating the DNA from the silica particles to obtain isolated DNA."

The DNA yield obtained according to the methods described herein may be approximately equal to or better than the yield obtained using preexisting commercial kits. About 1 µL of each DNA sample (in the elution buffer) may be sufficient to perform PCR. All reagents may be completely used, such that no waste remains, and all plates washed and re-used. The quantity and concentration of DNA may be suitable for a vary of settings and applications. For example, research institutions, industry laboratories, soil production laboratories, government laboratories, etc. may all implement the methods herein. DNA from various microbial species can be isolated and analyzed, including but not limited to: *Bacillus anthracis*, *Bacillus subtilis*, and *Streptomyces* species.

As used herein, the term "about" modifying, for example, the quantity of a component in a composition, concentration, and ranges thereof, employed in describing the embodiments of the disclosure, refers to variation in the numerical quantity that can occur, for example, through typical measuring and handling procedures used for making compounds, compositions, concentrates or use formulations; through inadvertent error in these procedures; through differences in the manufacture, source, or purity of starting materials or components used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities.

Similarly, it should be appreciated that in the foregoing description of example embodiments, various features are sometimes grouped together in a single embodiment for the purpose of streamlining the disclosure and aiding in the understanding of one or more of the various aspects. These methods of disclosure, however, are not to be interpreted as reflecting an intention that the claims require more features than are expressly recited in each claim. Rather, as the following claims reflect, inventive aspects lie in less than all features of a single foregoing disclosed embodiment, and each embodiment described herein may contain more than one inventive feature.

Although the present disclosure provides references to preferred embodiments, persons skilled in the art will recognize that changes may be made in form and detail without departing from the spirit and scope of the invention.

What is claimed is:

1. A method of extracting and isolating DNA (deoxyribonucleic acid) from a soil sample, the method comprising:

mixing the soil sample with a sonication buffer to form a soil suspension, the sonication buffer comprising cTAB (cetrimonium bromide);

sonicating the soil suspension to lyse microbial cells within the soil sample and form a lysis suspension within a first centrifuge plate or tube;

centrifuging the first centrifuge plate or tube to separate solid soil debris from DNA released from the microbial cells, wherein the DNA released from the microbial cells is contained in a DNA supernatant;

preparing a second centrifuge plate or tube to receive the DNA supernatant from the first centrifuge plate or tube by washing and resuspending silica powder with water to form a silica solution comprised of silica particles, the silica solution contained in the second centrifuge plate or tube, different than the first centrifuge plate or tube, wherein the silica particles and water are present in the silica solution at a ratio of 1:1, and wherein the first centrifuge plate or tube and the second centrifuge plate or tube do not comprise disposable bead tubes, membranes, or spin columns;

transferring the DNA supernatant from the first centrifuge plate or tube directly to the second centrifuge plate or tube to admix the DNA supernatant with the silica solution, wherein the DNA released from the microbial cells binds to the silica particles;

washing non-DNA debris from the silica particles in the second centrifuge plate or tube;

isolating the DNA from the silica particles; and eluting the isolated DNA in an elution buffer in the second centrifuge plate or tube.

2. The method of claim 1, wherein mixing the soil sample with a sonication buffer is performed in an 8-mL well of a multi-well plate.

3. The method of claim 1, wherein the soil sample comprises between about 250 and about 750 mg of soil, inclusive.

4. The method of claim 1, wherein the soil sample comprises a mixture of soil and water.

5. The method of claim 4, wherein about 2 mL of the mixture of soil and water is mixed with the sonication buffer.

6. The method of claim 1, wherein admixing the DNA supernatant with the silica solution comprises admixing the DNA supernatant with a mixture of 200 µL of the silica solution and 1 mL of 6M guanidine thiocyanate.

7. The method of claim 1, wherein washing non-DNA debris from the silica particles comprises resuspending and centrifuging the silica particles in a wash buffer two or more times.

8. The method of claim 1, wherein the sonication buffer comprises about 2% w/v cTAB.

9. A method of extracting and isolating microbial DNA from a plurality of soil samples, the method comprising:

adding 2 mL of each of the plurality of soil samples into separate wells within a multi- well plate;

mixing each soil sample with a sonication buffer to form a soil suspension, the sonication buffer comprising cTAB;

sonicating the soil suspension to lyse microbial cells within each of the plurality of soil samples and form a lysis suspension;

centrifuging the multi-well plate to separate solid soil debris from DNA released from the microbial cells, wherein the DNA released from the microbial cells is contained in a DNA supernatant within each well of the multi-well plate;

preparing a second multi-well plate to receive the DNA supernatant from the first multi-well plate by washing and resuspending silica powder with water to form a silica solution comprised of silica particles, the silica solution aliquoted into separate wells within the second multi-well plate, wherein the silica solution comprises a 1:1 mixture of silica particles and water, wherein the multi-well plate and the second multi-well plate do not comprise disposable bead tubes, membranes, or spin columns;

transferring each DNA supernatant from the multi-well plate directly to the second multi- well plate with the silica solution, wherein the DNA released from the microbial cells binds to the silica particles;

washing non-DNA debris from the silica particles in the second multi-well plate; and separating the DNA from the silica particles to obtain isolated DNA.

10. The method of claim 9, wherein each of the separate wells within the multi-well plate holds 8 mL of liquid.

11. The method of claim 9, wherein the multi-well plate includes 24 wells.

12. The method of claim 9, wherein the sonication buffer comprises NaCl, PVP, TE buffer, RNase A, and about 2% w/v cTAB.

13. The method of claim 9, wherein each of the plurality of soil samples comprises a 1:1 mixture of soil and water.

14. The method of claim 9, wherein each of the plurality of soil samples comprises about 500 mg of soil.

15. The method of claim 9, wherein admixing each DNA supernatant with the silica solution comprises admixing the DNA supernatant with a mixture of 200 µL of the silica solution and 1 mL of 6M guanidine thiocyanate.

16. The method of claim 1, wherein the silica solution consists of a mixture of silica powder, water, and guanidine thiocyanate.

17. A method of extracting and isolating DNA (deoxyribonucleic acid) from a soil sample, the method comprising:

mixing the soil sample with a sonication buffer to form a soil suspension, the sonication buffer comprising cTAB (cetrimonium bromide);

sonicating the soil suspension to lyse microbial cells within the soil sample and form a lysis suspension within a first centrifuge plate or tube;

centrifuging the first centrifuge plate or tube to separate solid soil debris from DNA released from the microbial cells, wherein the DNA released from the microbial cells is contained in a DNA supernatant;

preparing a second centrifuge plate or tube, different than the first centrifuge plate or tube, to receive the DNA supernatant from the first centrifuge plate or tube by washing and resuspending silica powder with water to form a silica solution comprised of silica particles, the silica solution contained in the second centrifuge plate or tube, wherein the silica particles and water are present in the silica solution at a ratio of 1:1, and wherein the silica solution is free of other binding solutions;

transferring the DNA supernatant from the first centrifuge plate or tube directly to the second centrifuge plate or tube to admix the DNA supernatant with the silica solution, wherein the DNA released from the microbial cells binds to the silica particles, and wherein the first centrifuge plate or tube and the second centrifuge plate or tube do not comprise disposable bead tubes, membranes, or spin columns;

washing non-DNA debris from the silica particles;

isolating the DNA from the silica particles; and eluting the isolated DNA in an elution buffer.

18. The method of claim 17, wherein the soil sample comprises between about 250 and about 750 mg of soil, inclusive.

19. The method of claim 17, wherein the soil sample comprises a mixture of soil and water.

20. The method of claim 17, further comprising mixing the soil sample with water before mixing the soil sample with the sonication buffer.

* * * * *

UNITED STATES PATENT AND TRADEMARK OFFICE
CERTIFICATE OF CORRECTION

| | | |
|---|---|---|
| PATENT NO. | : 11,725,202 B2 | Page 1 of 1 |
| APPLICATION NO. | : 16/165847 | |
| DATED | : August 15, 2023 | |
| INVENTOR(S) | : Elizabeth Buescher, Brad Roetman and Peter Zervos | |

It is certified that error appears in the above-identified patent and that said Letters Patent is hereby corrected as shown below:

In the Specification

In Column 4, Line 14 delete ""5 µg/L"" and replace with --5 µg/µL--
In Column 5, Line 58, delete ""5 µg/L"" and replace with --5 µg/µL--
In Column 6, Line 5, delete ""4816xg"" and replace with --4816 x g--
In Column 6, Line 29 insert --®-- after FILM Signed and Sealed this
Twentieth Day of February, 2024

Katherine Kelly Vidal
*Director of the United States Patent and Trademark Office*